United States Patent
Zorbach

(10) Patent No.: US 10,067,052 B2
(45) Date of Patent: *Sep. 4, 2018

(54) APPARATUS FOR OPTICAL IN-SITU GAS ANALYSIS

(71) Applicant: SICK AG, Waldkirch (DE)

(72) Inventor: Ralf Zorbach, Waldkirch (DE)

(73) Assignee: SICK AG, Waldkirch (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/630,281

(22) Filed: Jun. 22, 2017

(65) Prior Publication Data

US 2017/0370829 A1 Dec. 28, 2017

(30) Foreign Application Priority Data

Jun. 24, 2016 (DE) .......................... 10 2016 111 657

(51) Int. Cl.
*G01N 21/00* (2006.01)
*G01N 21/31* (2006.01)
(Continued)

(52) U.S. Cl.
CPC .............. *G01N 21/31* (2013.01); *B01D 53/30* (2013.01); *B01F 15/00175* (2013.01);
(Continued)

(58) Field of Classification Search
CPC .......... G01N 1/10; G01N 15/00; G01N 19/00; G01N 21/00; G01N 21/01; G01N 21/03; G01N 21/31; G01N 21/35; G01N 21/39; G01N 21/59; G01N 21/61; G01N 21/85; G01N 21/276; G01N 21/3504; G01N 21/8507; G01N 33/00; G01N 33/0036; G01B 9/00; G02B 5/02; B01D 53/30; B01F 15/00; B01F 15/06; B01F 2015/062;
(Continued)

(56) References Cited

U.S. PATENT DOCUMENTS

| | | | | |
|---|---|---|---|---|
| 3,860,818 A | * | 1/1975 | Stalder ................... | G01N 21/85 250/343 |
| 4,549,080 A | * | 10/1985 | Baskins ............. | G01N 21/3504 250/338.1 |
| 2008/0168851 A1 | * | 7/2008 | Lopez .................. | G01N 1/2258 73/866.5 |

OTHER PUBLICATIONS

Office Action dated Mar. 7, 2017 issued in corresponding German Application No. 10 2016 111 657.2.

* cited by examiner

*Primary Examiner* — Jamil Ahmed
(74) *Attorney, Agent, or Firm* — Nath, Goldberg & Meyer; Jerald L. Meyer

(57) ABSTRACT

The invention relates to an apparatus for the optical in-situ gas analysis that comprises a housing; a measuring lance whose one, first end is connected to the housing and whose other, second end projects into the gas to be measured; a light transmitter arranged in the housing whose light is conducted into the measuring lance and is reflected onto a light receiver by a reflector arranged at the second end, wherein the optical path defines an optical measurement path within the measuring lance; a gas-permeable filter through which the gas to be measured moves into the measurement path; and an evaluation device for evaluating received light signals of the light receiver. To provide an improved apparatus with which the problem of the condensate formation can be counteracted better, provision is made that the measuring lance has an agitation apparatus for agitating the gas in the measuring lance.

3 Claims, 1 Drawing Sheet

(51) Int. Cl.
  *B01D 53/30* (2006.01)
  *B01F 15/00* (2006.01)
  *B01F 15/06* (2006.01)
  *G01N 33/00* (2006.01)
(52) U.S. Cl.
  CPC ........ *B01F 15/00363* (2013.01); *B01F 15/06* (2013.01); *G01N 33/0036* (2013.01); *B01F 2015/062* (2013.01)
(58) Field of Classification Search
  CPC . B01F 15/00175; B01F 15/00363; G01J 1/00; G01J 1/02; G01J 1/04; G01J 5/02; G01D 21/00
  See application file for complete search history.

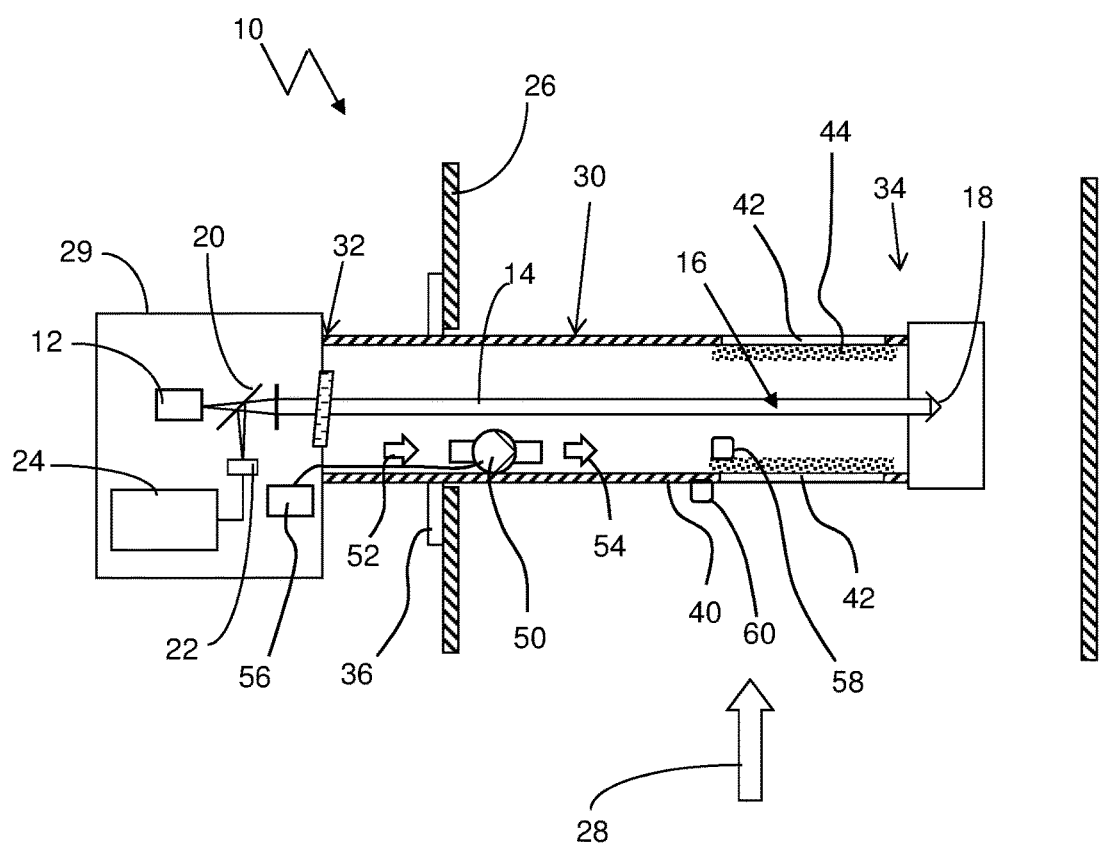

APPARATUS FOR OPTICAL IN-SITU GAS ANALYSIS

The invention relates to an apparatus for optical in-situ gas analysis in accordance with the preamble of claim 1.

Specific gas portions, e.g. hydrogen sulfide, carbon monoxide, SO2, NH3, NO, NO2, HCl, HF or the like, are measured by means of optical transmission or light scattering using such apparatus. The concentration of these gas portions is typically determined in this respect.

Fields of application are, for example, emission measurements of industrial plant in which the exhaust gases in an exhaust gas passage have to be monitored with respect to their content of specific molecular compounds. The gas flows to which the optoelectronic apparatus is exposed to measure the desired gas portions are frequently characterized by high particulate loads such as smoke, dusts or other aerosols. These high particulate loads cause strong light absorption and/or strong light scattering that greatly impairs/impair the actual measurement and even makes/make it impossible. Hydrogen sulfide, for example, has a very wide absorption and also ultrafine dust. It is then no longer possible to distinguish whether the absorption is due to the hydrogen sulfide or to the dust.

It is known (e.g. U.S. Pat. No. 4,549,080) to provide filters that comprise a length of pipe of porous material in whose interior the measurement path is located to keep out such particulates. Due to the porous structure, the gas to be measured can admittedly move into the measurement path; however, particulates such as smoke, dusts or aerosols can be kept out depending on the pore size.

To avoid disturbing condensation phenomena in the interior of the measuring lance, in particular with wet measuring gases, the optical boundary layers are heated by means of ring-type heating devices in accordance with U.S. Pat. No. 4,549,080. This is complex and expensive and does not prevent condensation at other points within the measuring lance. Additional condensate outlets are thus necessary that are, however, not simple to implement since the measuring lance should be designed such that the gas only enters into the measuring lance through the filter. As a rule, when condensate is present, which is frequently the case in saturated, wet exhaust gases, the measuring lance has to be replaced or at least serviced.

Starting from this prior art, it is the object of the invention to provide an improved apparatus with which the problem of condensate formation can be counteracted better.

This object is satisfied by an apparatus having the features of claim 1.

The apparatus in accordance with the invention for the optical in-situ gas analysis comprises a housing; a measuring lance whose one, first end is connected to the housing and whose other, second end projects into the gas to be measured; a light transmitter arranged in the housing whose light is conducted into the measuring lance and is reflected onto a light receiver by a reflector arranged at the second end, wherein the optical path defines an optical measurement path within the measuring lance; a gas-permeable filter through which the gas to be measured moves into the measuring lance; and an evaluation device for evaluating received light signals of the light receiver. In accordance with the invention, the measuring lance has an agitating apparatus for agitating the gas in the measuring lance.

It has been recognized that water in the measuring lance arises due to condensation at the inner filter wall. The condensate arises in the brief periods of time in which gas temperature fluctuations are present, that is when the temperature of the inner filter wall is lower than the dew point temperature of the gas. With increased temperature fluctuations about the dew point, more condensate arises that fills the filter. One explanation is the different speed of the gas exchange and the temperature line. While the gas exchange is intentionally fast so that the same gas is present as fast as possible in the measurement path as in the exhaust gas passage, the temperature line through the porous filter is not so fast. Warm, humid air then comes into contact with a still cold inner wall and condensation begins.

Due to the agitation of the gas in the measuring lance in accordance with the invention, a fast temperature equalization and a brisk mixture or exchange of the gas in the different regions are achieved in an extremely fast manner, in particular also at critical points such as the inner filter wall.

No complex and/or expensive construction is required. Condensate outlet paths or pumping down paths whose function would depend on the installation position of the lance are not necessary. The servicing and repair friendliness is substantially increased overall.

The agitation of the measuring gas in accordance with the invention also has the positive secondary effect that the gas exchange between the gas in the exhaust passage and the gas in the measuring line is accelerated due to the internal agitation and the response time of the apparatus in accordance with the invention is improved.

In a further development of the invention, the agitation apparatus is formed in a very constructionally simple manner as a fan.

When the temperature at the inner filter side is detected by a temperature measuring sensor, a control of the fan can take place in dependence on this temperature.

The gas temperature is preferably also detected by temperature sensors that are present as standard. The condensate formation can be avoided if either the temperature at the inner filter wall is kept higher than the dew point of the measuring gas. This difference can be evaluated in an agitation apparatus control device and the agitation apparatus can be controlled in dependence on the temperature difference at the inner filter side and on the gas temperature. The agitation apparatus switches on from a certain threshold difference temperature onward. If the temperature difference falls below the fixed threshold value, an equalized state from internal to external can be assumed and the agitation apparatus switches off. This also increases the service life of the pump.

If the movement of the gas by the agitation is also accompanied by a heating by means of a heating device, the droplet/condensate formation is avoided even more certainly.

The invention will be explained in detail in the following with reference to an embodiment and to the drawing. There is shown in the drawing:

FIG. 1 a schematic representation of an embodiment of the apparatus for the optical in-situ gas analysis in a gas flow.

An optoelectronic apparatus 10 in accordance with the invention for the optical in-situ gas analysis of a gas flow 28 that is conducted in an exhaust gas passage 26 has a light transmitter 12 that transmits a transmitted light beam 14 in an embodiment shown in FIG. 1. The transmitted light beam 14 defines a measurement path 16 and is received by a light receiver 22 after reflection at a retroreflector 18 and at a beam splitter 20. The light receiver 22 generates received signals in dependence on the incident light that are evaluated in an evaluation device 24, for example to determine the concentration of a component of the measuring gas.

Such an optoelectronic apparatus 10 is configured in this embodiment as a transmissiometer such that the intensity of the light radiating through the measurement path 16 is measured by the light receiver 22. As a rule, the light transmitter 12 is tuned to a specific wavelength which is absorbed by a gas proportion to be inspected, for example hydrogen sulfide. A statement can then be made via the light received at the light receiver 22 as to how high the concentration of the gas proportion of interest is in the gas flow 28 which is conducted in the exhaust gas passage 26.

The optoelectronic apparatus 10 comprises a housing 29 having a measuring lance 30 whose one, first end 32 is connected to the housing 29 and whose other, second end 34 projects into the exhaust gas passage 26 and thus into the gas 28 to be measured. The housing 29 and the measuring lance 30 are fixed to a wall of the exhaust gas passage 26 via a fastening flange 36.

The optoelectronic units such as the light transmitter 12, light receiver 22 and evaluation device 24 are arranged in the housing 29 and the light is conducted through the measurement path 16 in the measuring lance 30. The retroreflector 18 is held in a reflector housing at the second end 34 of the measuring lance 30.

The measuring lance 30 has a pipe 40 that extends over the total length of the measuring lance 30 and is fixed at its one end to the housing 29 and holds the retroreflector 18 at its other end. The outer pipe 40 has openings 42 in the region of the outer pipe 40 that projects into the exhaust gas passage 26 such that portions of the gas flow 28 can move into the measurement path 16.

The gas flow 28 that is conducted in the exhaust gas passage 26 and that is only indicated by an arrow 28 can be loaded with particulates, for example dust, smoke or other aerosols, with the particulates disturbing the actual optical measurement over the measurement path 16. To keep the particulates out of the measurement path 16, a gas-permeable filter 44, preferably of porous material, is provided at least in the region of the openings 42. The openings 42 in the outer tube 40 in this embodiment are configured as two larger slit openings 42 through which the measuring gas 28 can enter and exit the filter 44.

In accordance with the invention, an agitation apparatus 50 is arranged in the measuring lance 30 and the gas in the measuring lance 30 can be agitated by it as is indicated by the arrows 52 and 54. The agitation apparatus 50 is preferably configured as a fan and is controlled by an agitation apparatus control device 56. The agitation apparatus control device 56 is connected in a manner not shown to a first temperature measuring sensor 58 that detects the temperature at the inner side of the filter 44 and is connected to a second temperature measuring sensor 60 that detects the temperature of the gas in the exhaust gas passage 26.

A threshold temperature difference between the temperature at the inner side of the filter 44 and the temperature of the gas can be set at the agitation apparatus control device 56, above which threshold temperature the agitation apparatus 50 is intended to work.

A heating device, not shown, for heating the measuring gas in the measuring lance 30 can be integrated into the agitation apparatus 50 so that the gas is not only agitated, but is rather simultaneously also heated.

In a further embodiment, not shown, of the apparatus 10 in accordance with the invention, said apparatus is configured in two parts and has a first apparatus part that can have the same design as that of the first embodiment and has a second apparatus part that is arranged at the oppositely disposed side of the flue 26 and in which, for example, the reflector could be arranged. In this second apparatus part, a second light receiver can also be arranged that is arranged such that it can, for example, receive forward scattered light so that a concentration evaluation of gas portions can also be carried out in accordance with the principle of scattered light measurement with this measuring unit. The scattered light received by the receiver is evaluated in a second evaluation device for this purpose. This embodiment having two parts at oppositely disposed sides of the exhaust gas passage is also called "cross-duct".

The invention claimed is:

1. An apparatus for optical in-situ gas analysis, comprising:
   a housing;
   a measuring lance having a first end and a second end, the first end being connected to the housing and the second end projecting into a gas to be measured, the measuring lance having an agitation apparatus for agitating the gas in the measuring lance;
   a light transmitter for transmitting light, the light transmitter being arranged in the housing, the light from the light transmitter being conducted into the measuring lance and being reflected by a reflector arranged at the second end onto a light receiver, and the transmitted light defines an optical measurement path within the measuring lance;
   a gas-permeable filter through which the gas to be measured moves into the optical measurement path;
   an evaluation device for evaluating received light signals of the light receiver;
   a temperature measuring sensor arranged at an inner side of the gas-permeable filter; and
   an agitation apparatus control device for controlling the agitation apparatus dependent on a temperature difference of a temperature at the inner side of the gas-permeable filter and a gas temperature of the gas.

2. The apparatus for optical in-situ gas analysis in accordance with claim 1, wherein the agitation apparatus is configured as a fan.

3. An apparatus for optical in-situ gas analysis, comprising:
   a housing;
   a measuring lance having a first end and a second end, the first end being connected to the housing and the second end projecting into a gas to be measured, the measuring lance having an agitation apparatus for agitating the gas in the measuring lance, the agitation apparatus having a heating device for heating the gas in the measuring lance;
   a light transmitter for transmitting light, the light transmitter being arranged in the housing, the light from the light transmitter being conducted into the measuring lance and being reflected by a reflector arranged at the second end onto a light receiver, and the transmitted light defines an optical measurement path within the measuring lance;
   a gas-permeable filter through which the gas to be measured moves into the optical measurement path; and
   an evaluation device for evaluating received light signals of the light receiver.

* * * * *